United States Patent [19]
Brenholdt

[11] Patent Number: 4,760,271
[45] Date of Patent: Jul. 26, 1988

[54] APPARATUS AND PROCESS FOR MEASURING FORMATION AND ROUGHNESS OF A PAPER WEB

[75] Inventor: Irving R. Brenholdt, Stratford, Conn.

[73] Assignee: Champion International Corporation, Stamford, Conn.

[21] Appl. No.: 843,588

[22] Filed: Mar. 25, 1986

[51] Int. Cl.⁴ ............................................. G01N 21/32
[52] U.S. Cl. ...................... 250/571; 250/572; 250/562; 250/559; 356/430
[58] Field of Search ............ 250/571, 559, 562, 563, 250/572; 356/429, 430, 431, 73

[56] References Cited

U.S. PATENT DOCUMENTS

| | | | |
|---|---|---|---|
| 3,693,021 | 9/1972 | Lake, Jr. et al. | 250/562 |
| 3,841,761 | 10/1974 | Selgin | 250/562 |
| 4,019,066 | 4/1977 | Lucas et al. | 356/371 |
| 4,092,068 | 5/1978 | Lucas et al. | 250/563 |
| 4,145,140 | 3/1979 | Fujii | 356/371 |
| 4,146,330 | 3/1979 | Belden, Jr. | 356/445 |
| 4,213,708 | 7/1980 | Lucas | 250/559 |
| 4,222,064 | 9/1980 | Lodzinski | 356/429 |
| 4,248,533 | 2/1981 | Shimada | 250/572 |
| 4,644,174 | 2/1987 | Ouellette et al. | 250/572 |

*Primary Examiner*—Edward P. Westin
*Assistant Examiner*—Charles F. Wieland
*Attorney, Agent, or Firm*—Evelyn M. Sommer

[57] ABSTRACT

An apparatus and process are disclosed for examining a moving web of paper to determine the optical parameter of "formation" and the physical parameter of "roughness". The apparatus includes an optical system which forms an area of the web, with a first light source directing light through the moving web area from a back surface thereof, and a second light source directing light obliquely to the web area from the front surface thereof. A signal processing device determines the root-mean-square of the quotient resulting from the difference in received radiation from two spatially adjacent areas of the detectors divided by the sum of the received radiation from four spatially adjacent areas of said detectors to provide an output signal corresponding to formation or roughness of the paper web.

15 Claims, 4 Drawing Sheets

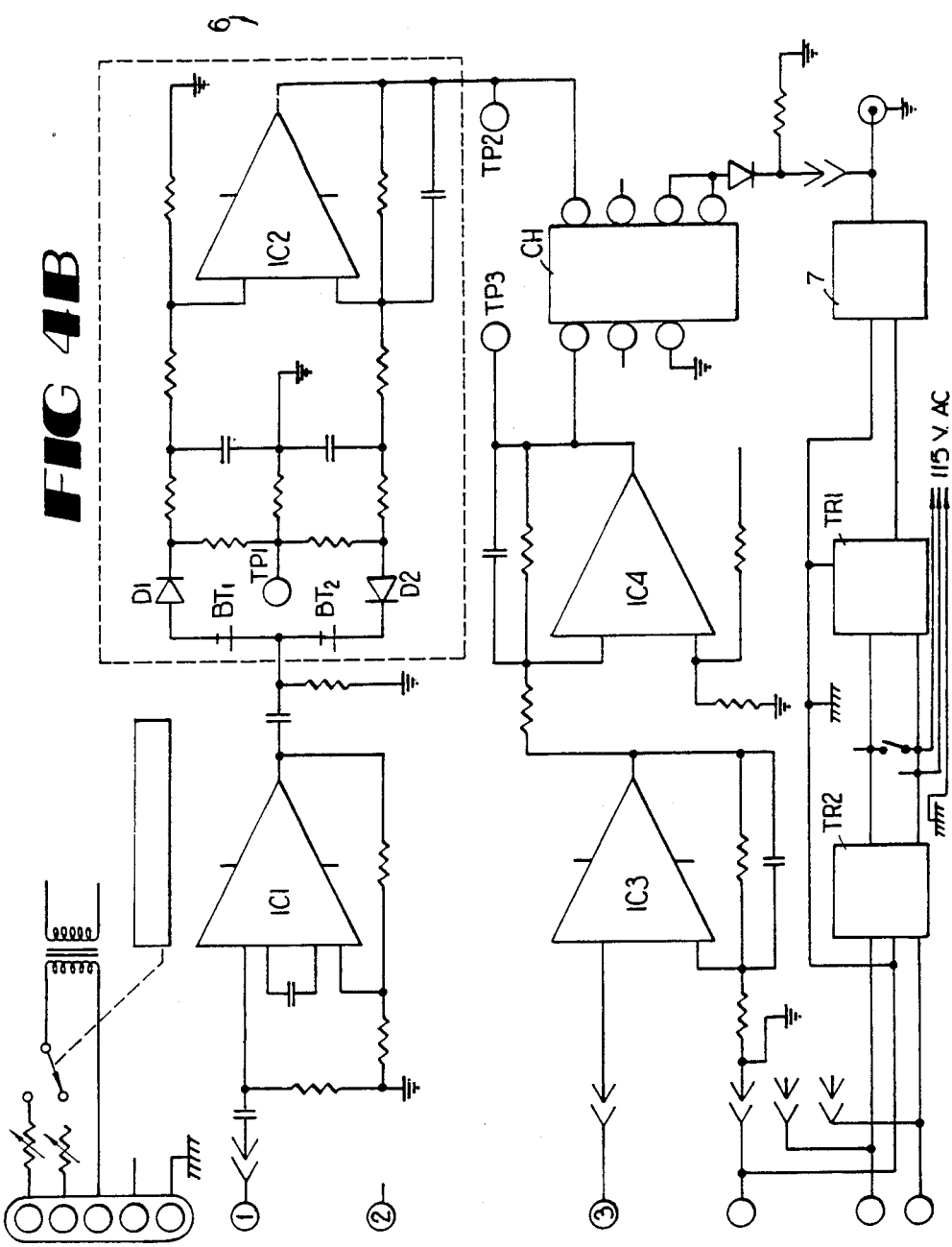

APPARATUS AND PROCESS FOR MEASURING FORMATION AND ROUGHNESS OF A PAPER WEB

BACKGROUND OF THE INVENTION

The present invention relates to the art of paper-making and more particularly to a system capable of sensing formation and/or roughness of a paper web during production.

In the past, the examination of paper or paperboard webs during production for sensing roughness has been primarily through the use of mechanical devices such as by means of a stylus riding on the surface of the web to sense the surface roughness. Optical systems have also been used for determining formation but for the most part not on-line with the moving web. Rather, web samples have been taken from the production line and examined off-line, typically by sensing light transmitted through the sample from the interior of a mounting drum which is rotated.

An example of a prior art optical system for use in examining a moving paper web during production for defects including holes and wrinkles in the web is found in U.S. Pat. No. 4,160,913 entitled "WEB SCANNING APPARATUS" which issued on July 10, 1979 to the present applicant. In the disclosed system of U.S. Pat. No. 4,160,913 a flying spot is employed to scan the web for determining the two edges and defects, including holes and wrinkles, in the web. A detector senses the changes in reflected illumination, and a circuit discriminates between a dark signal which yields a positive then negative going pulse to indicate a hole, and a light signal which yields a negative then positive going pulse to indicate a wrinkle. While this prior system is very useful in detecting holes and wrinkles, it is important in the manufacture of paper to provide detecting means for the on-line scanning operation determination of roughness and formation of the paper web.

Accordingly, the present invention is directed to providing an improved optical system for paper testing, either on-line or in a laboratory, which can accurately measure the formation and roughness of paper webs.

It is a further object of the present invention to provide a process and apparatus for measuring formation and roughness of a paper web while on-line irrespective of web velocity and optical source energy variations during the testing operation.

SUMMARY OF THE INVENTION

The present invention is embodied in a system for analyzing the quality of paper in production, using a time shared optical sensing apparatus that, with individual or time-sharing measurements and data, selectively provides an indication of the optical parameter of formation or the physical parameter of surface roughness of a moving web for analysis or display. The system comprises a light source in combination with an optical radiation detector disposed in a focal plane for receiving an image of an illuminated area of the web being examined at a location along the path of movement of the web. The light source directs light through the web when measuring formation, and reflects light from the web surface when measuring roughness. The illuminated area is divided into four adjacent equal-sized portions, typically one square millimeter each. The detector is in the form of a quadrant sensor with four adjacent equal-sized light sensitive regions or sectors, each electrically connected to circuitry for analyzing the received light energy. The light energy passing through, or reflected from, each of the four portions on the web will vary dynamically during movement of the web in accordance with the characteristics or qualities of the paper web.

In analyzing the sensed light energy, the differences between the level of energy received at two selected adjacent sectors transversly disposed with respect to the axis of movement of the web will produce an alternating signal proportional to either formation or roughness depending upon whether the light is transmitted or reflected by the web. When this alternating difference signal is converted to direct current and integrated over a short period, e.g. two seconds, the resulting signal will be independent of the effect of web velocity beyond a minimal threshold velocity. A direct current signal, resulting from the sum of the output signals from all four sectors of the sensor, is also produced, and is proportional to the received light energy but independent of web velocity and web quality. These difference and sum signals are continuously input to a signal processor and the output of the signal processor provides a reliable indication of the web characteristics, formation and/or roughness, being analyzed.

BRIEF DESCRIPTION OF THE DRAWINGS

FIG. 4B is a schematic diagram of the elements of a power supply, signal processing and display unit for use with the sensor system of FIG. 4A.

DETAILED DESCRIPTION OF THE PREFERRED EMBODIMENT

Figure 1:
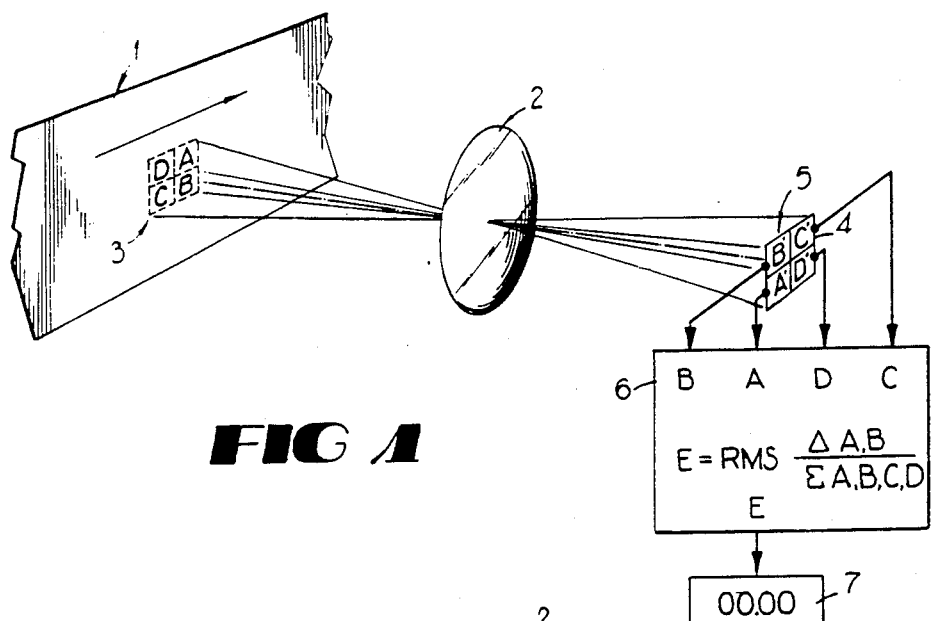
FIG. 1 is a diagrammatic view of the sensor system in accordance with the present invention.

FIG. 1 is an illustration of an on-line sensor system in accordance with the present invention. A suitable optical system or lens 2 focuses an image 5 of a field of view 3, on the surface of a moving paper web 1 during production, onto the quadrant sensor 4 of an electronic processing device 6. The field of view 3 may be divided into four adjacent equal-sized areas A,B,C,D typically one square millimeter each, and located at any convenient position along the path of movement of the web being produced following the drying operation so that the web qualities to be analyzed will not be subjected to any further production changes. The image 5 has its four areas A,B,C,D appropriately directed by lens 2 onto the four adjacent and equal-sized light sensitive sectors of the quadrant sensor 4. Output signals from the sensor 4, produced by the dynamically varying intensity of the light energy in the four areas A,B,C,D, due to variations in web characteristics, are processed and analyzed in the processing device 6 and an indication of the results may be displayed on a suitable display 7. As will be more fully explained, difference signals, e.g. A−B, and a sum signal A+B+C+D, are compared in the processor 6, which produces an output that indicates the measurement of a characteristic or quality of the paper making up the web 1. Alternatively, any two other areas, e.g. A,D, may be used to provide the difference signal.

Figure 2A:
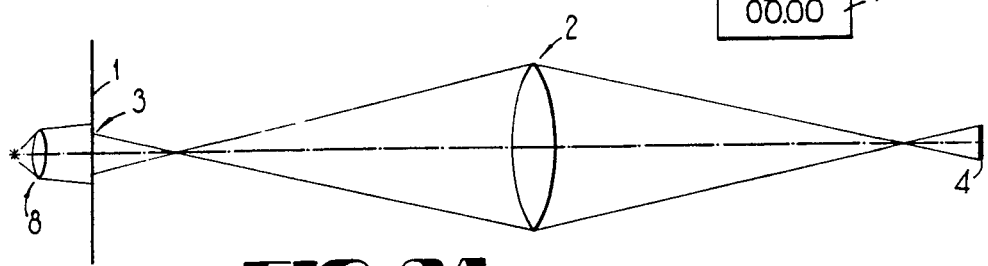
FIG. 2A is a schematic view illustrating the arrangement of the optical elements of the system of FIG. 1 when used for detecting the formation of a moving web.

The characteristics most suitable for measurement by the system are "formation" and "roughness". Formation is a quality of the paper affected by the relationship of the fibers making up the paper, such as their distribution and orientation, which will vary the optical integrity and uniformity of the web. Roughness is a quality related to the surface smoothness of the paper. Web illumination to produce the image 5 will differ depending on which of the two cited characteristics is to be analyzed. The illumination arrangement for the formation measurement mode is shown in FIG. 2A. For example, a light source 8, having an integral projection lens, is used to project light energy onto the back or under-side of the web 1 for transmission through the paper web 1 and emersion within the field of view 3. The lens 2 acts to focus the light energy from the field of view 3 onto the face of the quadrant sensor 4. The amount of light energy passing through the paper will depend on the fiber structure passing through the field of view at any instant.

Figure 2B:
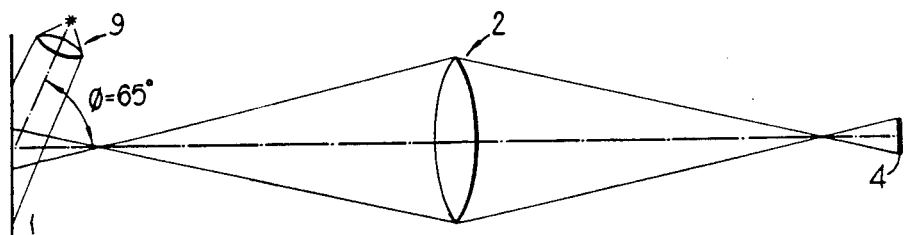
FIG. 2B is a schematic view illustrating the arrangement of the optical elements of the system of FIG. 1 when used for detecting the surface roughness of a moving web.

The manner of web illumination for the surface roughness measurement mode is shown in FIG. 2B. A light source 9, having an integral projection lens, directs light obliquely against the surface of the web 1 at the field of view 3. The axis of the light rays is preferably displaced about 65°±10° off the axis of lens 2 which will direct any stray light energy reflected from irregularities, such as bumps and ridges, on the web surface to the areas on the quadrant sensor 4. If the surface of the web is very smooth, the impinging light rays will all be reflected away from the optical axis of lens 2 and no light energy will be directed onto the sensor 4. Consequently, the amount of light energy falling on the sensor 4 will be directly proporational to the roughness of the web surface.

It will be seen from FIG. 2A and FIG. 2B that the optical system, including lens 2, and the quadrant detector 4 arrangement may be the same for both modes if the front or upper surface of the web is being tested. The lens 2 and sensor 4 may be disposed on the same axis but on the opposite side of the web 1 if the back or underside is to be monitored. The intensity or level of the light energy may be the same for the two modes and may be adjusted by an initial setting of the power supply.

Figure 3A:
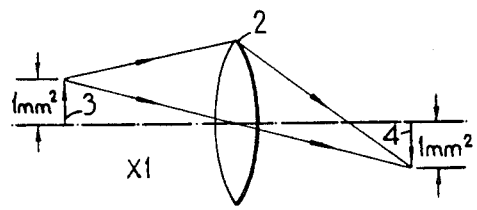
FIGS. 3A, 3B and 3C are schematic views illustrating three alternative optical arrangements for adjusting the size of the instantaneous area of a web being examined.
Figure 3B:
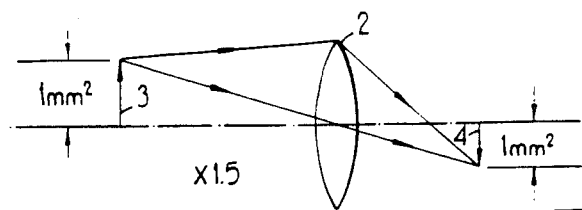
Figure 3C:
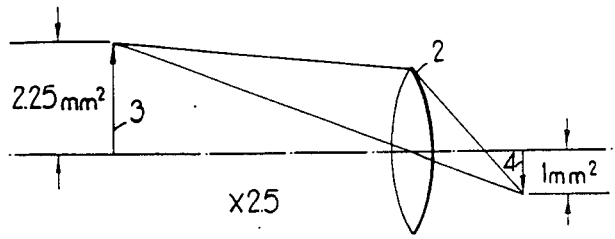

The size of the area of the field of view may be adjusted as seen in FIG. 3. The position and area of the quadrant sensor 4 remain fixed and the positions of the lens 2 and the web along the optical axis may be moved to increase or decrease the area of the field of view 3, as shown. However, since the web will usually be disposed on a production line, it will normally be more convenient to adjust the positions of lens 2 and sensor 4 to achieve the desired field size. Of course, a change in field size will result in a change in resolution of the image falling on the face of sensor 4. Details smaller than the field area will not be resolved as single details.

Figure 4A:
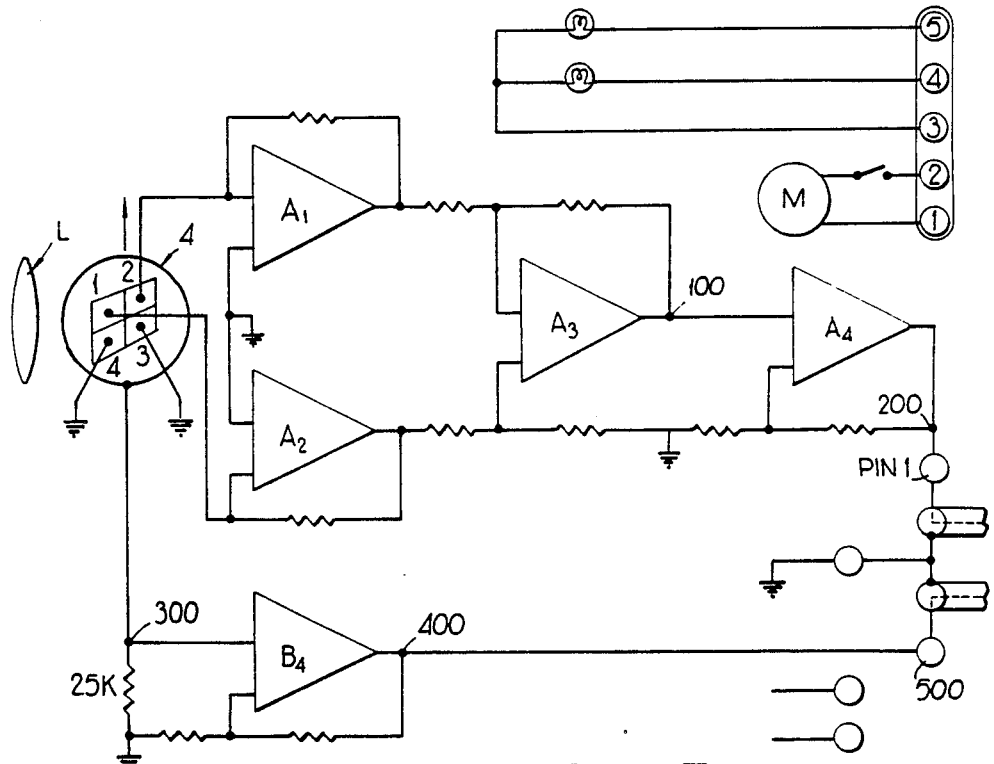
FIG. 4A is a schematic diagram of the elements of a sensor system in accordance with the invention.

An example of a suitable sensor assembly 4 is shown in FIG. 4A. An objective lens L directs the incoming light onto the four sectors of the quadrant sensor 4 for detection. As previously mentioned, it is desired to obtain difference signals from two of the sectors, e.g. A−B, as well as a sum signal from all four of the sectors. Accordingly, sectors C and D are grounded and the outputs of sectors A and B are applied respectively to A.C. pre-amplifiers $A_1$ and $A_2$ which provide matched or lowered impedance signals to differential amplifier $A_3$. The difference signal (A−B) from amplifier $A_3$ at point 100 is amplified by a line driver or amplifier $A_4$ by a factor of 10 and output at point 200 on pin 1 to the processor 6 (FIG. 4B). The sum signal is applied by means of a common lead to a 2.5K ohm resistance at point 300 for input to a D.C. amplifier $B_4$. The output (A+B+C+D) of amplifier $B_4$ at point 400 amplified by a factor of 100 is input at point 500 to pin 3 of the processor 6 (see FIG. 4B).

As seen in FIG. 4B, the dynamic A.C. signal from the sensor 4 is input to the processor from pin 1 to A.C. amplifier IC1. The A.C. output of amplifier IC1 is clipped by diodes $D_1$, and $D_2$, and shaped by D.C. differential amplifier IC2, which acts as a demodulator, to produce an RMS D.C. signal indicative of the fluctuations in the difference of the light energy falling on the sensor sectors A and B. This signal is the numerator input to a divider chip, CH e.g., a Burr Brown 4291K. The denominator input is the output of a D.C. amplifier IC4 which along with matching amplifier IC3 processes the sum signal input from pin 3. Appropriate capacitors are connected across amplifiers IC4 and IC2 to match the time constants of the numerator and denominator inputs to the divider CH.

Figure 7:
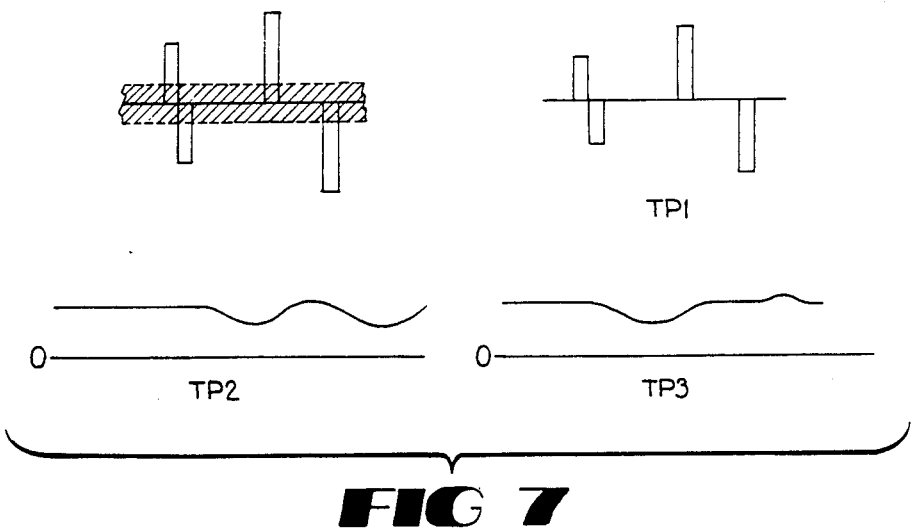
FIG. 7 illustrates the signal processing operation in the sensor system.

The forms of the signals appearing at test points TP1, TP2 and TP3 are shown in FIG. 7 by way of illustration. The output of IC1 may be of the form indicated in the upper left portion of FIG. 7. As it may not be desired to detect the smaller signal portions, the threshold level of detection may be adjusted to that of the dotted lines by the inclusion of bias voltages, shown as batteries $BT_1$ and $BT_2$ for clarity, in the demodulator circuit of FIG. 4B. As a result, the signal appearing at test point TP1 will be of the form shown. After shaping in differential amplifier IC2 the positive and negative signal spikes are converted to a positive D.C. signal having their RMS value and of the form appearing at test point TP2. The sum signal-denominator input appears at TP3 in FIG. 7.

The output of the divider CH, which will be the RMS value of the ratio of the difference signal (A−B) to the sum signal (A+B+C+D), is provided to a utilization device (FIG. 4B) such as a digital display 7 and/or a recorder (not shown) as an "index" of the parameter of the paper web being measured. A power supply for the system is also shown in FIG. 4B wherein A.C. line power is supplied to a +5 volt regulator TR1 for the digital display 7 and the light sources, and a ±15 volt regulator TR2 which provides the power to the sensor circuitry.

In operation, the system of the invention may be applied to the testing of a paper web moving along a production line, as noted above, or in a laboratory instrument embodiment such as the arrangement shown in FIG. 5, as more fully described hereinafter. In either case, the roughness of one or both surfaces of the paper web and/or its formation can be measured by the same essential combination of elements comprising an illuminating means, typically a light source, for illuminating a field of view along the path of movement of the sample, and a sensing system including a quadrant sensor and signal processor. The field of view is composed of four equal-sized areas A,B,C,D through which the moving sample passes. The qualities or composition of the paper making up the sample will cause the illumination from the areas A,B,C,D to vary appropriately with changes in paper quality. For example, if paper formation is being monitored and the illuminating light passes through the web sample, areas with more fibers will tend to block the light passage while areas with less fibers will pass a greater amount of light. Since the sample, either web or lab sample, is moved through the field of view, the illumination from a given area will vary instantaneously and this variation taken with that of an adjacent area will provide an indication of the change in paper formation. Similarly, if the light is directed obliquely to the surface of the sample, the light rays will be deflected by hills and valleys, contributing to roughness, at a different angle from the reflected rays from a smooth surface. The two exemplary situations are shown in FIG. 6 which depicts an enlarged cross-section of a web 1 with variations in formation and surface smoothness. The light from the surface of the sample within the field of view is directed by the lens 2 onto the face of the quadrant sensor which has four, equal-sized light-sensitive sectors which may or may not correspond in size to the four areas of the field of view. Irrespective of their size relationship however, the four areas A,B,C,D will have a correspondence respectively with the four sectors A', B',C',D' as shown in FIG. 1. Thus, as the light energy transmitted or reflected from the web surface varies dynamically with the paper characteristics in the four areas, corresponding signals will be produced by the responses of the four sectors to the light falling thereon.

The difference in received energy from the adjacent areas A and B by the sectors A', B' results in an alternating signal proportional to either formation or surface roughness depending upon whether the light is transmitted or reflected. When this alternating signal, representing A−B and proportional to received light energy, is converted to direct current and integrated over an appropriate period, e.g., two seconds, the result will be independent of web velocities greater than a minimum threshold, e.g., ten millimeters per second, which is essentially zero velocity in view of typical paper web velocities which exceed one meter per second.

By comparison, the sum of the energy falling on the sectors A',B',C',D' produces a direct current signal independent of sample velocity, directly proportional to the received energy, and independent of sample formation and roughness. When the two signals are input to processor 6, it performs the calculation E=RMS (A−B/A+B+C+D) continuously and presents the output E to an appropriate display 7 for observation.

The received light energy by the sectors for each of the measurement modes can be made approximately equal by one initial adjustment of the light source (see FIGS. 4A and 4B) intensities by means of adjusting the power supply.

Figure 5:
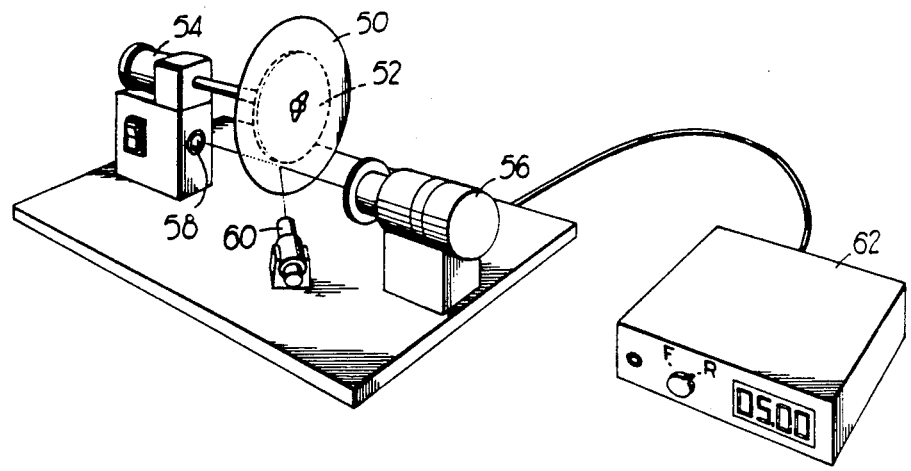
FIG. 5 shows an arrangement for implementing the system of the invention in a laboratory instrument embodiment.
Figure 6:
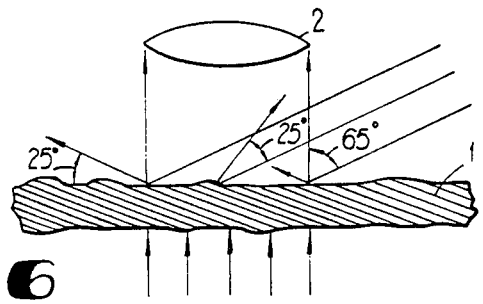
FIG. 6 is a diagrammatic view of the cross-section of a moving web illustrating the action of the transmitted and reflected light waves when examining the web formation and roughness, respectively.

In the laboratory instrument embodiment illustrated in FIG. 5, a test sample 50 of a paper web is mounted to a rotatable back plate 52 which is driven by a motor 54. The optical system and quadrant detector are disposed in a common housing 56, with the light source for determining formation being designated by numeral 58, and the light source for detecting roughness being designated by numeral 60. The output of device 56 is provided to the signal processor, power supply, and display device 62.

In summary, it will be seen that the invention provides an improved paper sample analyzing apparatus and process for individual or time-sharing analyzing apparatus and process for individual or time-sharing measurements and data relating to the optical parameter of formation and/or the physical parameter of surface roughness, of the paper including an optical system for forming an image of an area on the sample to be examined, either by light transmission through the moving sample or by light reflection obliquely off the surface depending upon the parameter to be measured. A light-sensitive detector disposed in the focal plane of the optical system receives the image and produces appropriate signals for input to a processing device which determines, as an output, the root-mean-square of the quotient resulting from the difference in received radiation from two spatially adjacent areas on the detector divided by the sum of the received radiation on the entire area of the detector. The outputs give an indication of variations in paper quality to permit on-line monitoring during paper production.

Although the present invention has been described and illustrated in its preferred embodiments with a certain degree of particularly, it is understood that the present disclosure has been made only by way of examples and that numerous changes in the details of the circuit elements may be resorted to without departing from the spirit and scope of the invention as defined by the following claims.

What is claimed is:

1. Apparatus for selectively measuring either the formation or roughness of a moving paper web comprising:

formation illumination means on one side of and substantially orthogonal to said paper web for illuminating an area on the paper web at a location along its path of movement;

optical means on the other side of the paper web for directing illumination transmitted through said area onto a focal plane on said other side of the paper web;

illumination detector means in said focal plane for receiving said transmitted illumination and producing signals proportional to the intensity thereof;

roughness illumination means on said other side of the paper web for directing illumination at an oblique angle with respect to a line normal to the plane of the paper web at said area when said formation illumination means is not operating;

said optical means directing illumination reflected from said area along a path normal to the plane of the paper web onto said focal plane;

said illumination detector means in said focal plane receiving said reflected illumination and producing signals proportional to the intensity thereof; and signal processing means for processing said signals detected by said illumination detector means when receiving illumination produced by said formation illumination means for measuring the formation of the paper web;

said signal processing means alternatively processing signals detected by said illumination detector means when receiving illumination produced by said roughness illumination means for measuring the roughness of the paper web.

2. Apparatus as in claim 1 wherein said signal processing means processes said signals by generating the root-mean-square of the quotient resulting from the difference in received illumination intensity from two spatially adjacent areas in said focal plane and the sum of the received illumination intensity from said two spatially adjacent areas and at least one additional spatially adjacent area at said illumination detector means.

3. Apparatus as in claim 1 wherein said roughness illumination means directs illumination at an angle of 65° with respect to a line normal to the plane of the paper web at said area.

4. Apparatus as in claim 2 wherein said focal plane has four adjacent areas and said illumination detector means comprises four adjacent sectors, two of which sectors correspond to said two spatially adjacent areas in said focal plane.

5. Apparatus as in claim 1 wherein said roughness illuminating means is directed at an oblique angle in the range of 55° to 75° with respect to a line normal to the plane of the paper web at said area.

6. Apparatus as in claim 1 further including display means connected to said signal processing means for providing a quantitative indication of the measured formation or roughness of the paper web.

7. Apparatus as in claim 2 wherein the said two spatially adjacent areas in said focal plane are disposed transverse to the direction of movement of the paper web.

8. Apparatus for the on-line continuous detection of the formation of a moving paper web comprising:

a formation light source disposed opposite one side of the plane of the moving paper web for illuminating an area of said paper web, said area including four adjacent portions;

optical means disposed opposite the other surface of said paper web for directing illumination from said area onto a focal plane;

illumination detector means in said focal plane for receiving said illumination and producing signals proportional to the intensity thereof, said illumination detector means comprising four adjacent sectors corresponding to said four adjacent portions in said illuminated area of said paper web, two spatially adjacent sectors corresponding to two spatially adjacent portions in said illuminated area of said paper web;

signal processing means responsive to said illumination detector means for determining the root-mean-square of the quotient resulting from the difference in received illumination intensity from said two spatially adjacent portions in said illuminated area of said paper web in said focal plane and the sum of the received illumination intensity from said four adjacent portions in said illuminated area of said paper web in said focal plane; and display means connected to said signal processing means for providing a continuous indication of the formation of the paper web.

9. Apparatus for selectively determining the roughness of one surface of a moving paper web or the formation of the paper web comprising:

a roughness light source directed at an oblique angle to said surface with respect to a plane through said surface of the moving paper web for illuminating an area including four adjacent portions;

a formation light source substantially orthogonally disposed opposite the opposite surface of the moving paper web for illuminating said area including four adjacent portions when said roughness light source is not operating;

optical means disposed opposite the side of said surface of the moving paper web illuminated by said roughness light source for directing illumination from said area onto a focal plane;

an illumination detector means in said focal plane for receiving said illumination produced by either said roughness light source or said formation light source and producing signals proportional to the intensity thereof, said illumination detector means including four adjacent sectors, two spatially adjacent sectors corresponding to two spatially adjacent portions of said illuminated area of the moving paper web;

signal processing means responsive to said illumination detector means for determining the root-mean-square of the quotient resulting from the difference in received illumination intensity from said two spatially adjacent portions of said illuminated area of the moving paper web in said focal plane and the sum of the received illumination intensity from said two spatially adjacent portions and two additional adjacent portions of said illuminated area of the moving paper web in said focal plane; and display means connected to said signal processing means for providing a continuous indication of either the surface roughness or the formation of the moving paper web.

10. Apparatus as in claim 9 wherein said roughness light source is directed at an angle in the range of 55° to 75° relative to the axis normal to the plane of the moving paper web.

11. Process for selectively detecting either the formation or the surface roughness of a moving paper web comprising:

illuminating an area of the moving paper web at a location along its path of movement either by transmitted light from one side of and through the moving paper web or by reflected light at an oblique angle to the plane of the surface on the other side of the moving paper web;

directing illumination from said area onto a focal plane;

measuring said illumination in the focal plane and producing signals proportional to the intensity thereof;

processing said signals to determine either the formation or the surface roughness of the moving paper web; and continuously displaying the resulting determination of either the formation or the surface roughness of the moving paper web.

12. Process as in claim 11 wherein said moving paper web is illuminated by a formation light source disposed spaced from and substantially orthogonally to said one side of the moving paper web, and the intensity of the illuminated area is measured on the opposite side thereof to determine the optical parameter of formation of the moving paper web.

13. Process as in claim 11 wherein the moving paper web is illuminated by a surface roughness light source directed at an oblique angle in the range of 55° to 75° relative to the axis normal to the plane of the surface of the moving paper web to determine the physical parameter of surface roughness of the moving paper web.

14. Process as in claim 13 wherein the surface roughness light source is directed at an angle of 65° relative to an axis normal to the plane of the moving paper web.

15. Process for making and testing a web of paper to determine its formation comprising:

preparing a continuous web of paper;

conveying the web of paper past a light source for illuminating an area on one side of the paper web at a location along its path of movement;

directing illumination transmitted through said area onto a focal plane on the other side of the paper web;

measuring said illumination in the focal plane and producing signals proportional to the intensity thereof;

processing said signals to determine the root-mean-square of the quotient resulting from the difference in received illumination intensity from two spatially adjacent illuminated portions of the web of paper in said focal plane and the sum of the received illumination in said focal plane from said two spatially adjusted illuminated portions of the web of paper and at least one additional illuminated portion adjacent said two spatially adjacent illuminated portions of the web of paper; and continuously displaying the resulting determination of the formation of the web of paper.

* * * * *